(12) United States Patent
Chun et al.

(10) Patent No.: US 8,846,215 B2
(45) Date of Patent: Sep. 30, 2014

(54) ORGANIC LIGHT-EMITTING DIODE AND METHOD FOR MANUFACTURING SAME

(71) Applicant: LG Chem, Ltd., Seoul (KR)

(72) Inventors: Minseung Chun, Daejeon (KR); Jungi Jang, Daejeon (KR); Sang Young Jeon, Daejeon (KR); Seong So Kim, Paju-s (KR); Chang Hwan Kim, Daejeon (KR); Hyungjin Lee, Daejeon (KR); Sung Kil Hong, Daejeon (KR); Kongkyeom Kim, Daejeon (KR); Yun Hwan Kim, Seoul (KR); Tae Yoon Park, Daejeon (KR); Jungoh Huh, Seoul (KR); Seongmi Cho, Gyeongju-si (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/052,293

(22) Filed: Oct. 11, 2013

(65) Prior Publication Data

US 2014/0061626 A1 Mar. 6, 2014

Related U.S. Application Data

(63) Continuation of application No. PCT/KR2012/009866, filed on Nov. 21, 2012.

(30) Foreign Application Priority Data

Dec. 23, 2011 (KR) .................. 10-2011-0141372

(51) Int. Cl.
| | | |
|---|---|---|
| *H01L 51/54* | (2006.01) | |
| *H01L 51/00* | (2006.01) | |
| *C07D 209/86* | (2006.01) | |
| *C07D 403/14* | (2006.01) | |
| *C07D 487/14* | (2006.01) | |
| *C07D 487/04* | (2006.01) | |
| *C09K 11/06* | (2006.01) | |
| *H05B 33/14* | (2006.01) | |
| *H05B 33/20* | (2006.01) | |

(52) U.S. Cl.
CPC ........ *H01L 51/0071* (2013.01); *H01L 51/0061* (2013.01); *H01L 51/0072* (2013.01); *C07D 209/86* (2013.01); *C07D 403/14* (2013.01); *C07D 487/14* (2013.01); *C07D 487/04* (2013.01); *C09K 11/06* (2013.01); *H05B 33/14* (2013.01); *H05B 33/20* (2013.01); *Y10S 428/917* (2013.01)
USPC ........... 428/690; 428/917; 313/504; 313/505; 313/506; 257/40; 257/E51.05; 257/E51.026; 257/E51.032; 548/304.1; 548/418; 548/440; 564/26; 564/426; 564/434

(58) Field of Classification Search
None
See application file for complete search history.

(56) References Cited

U.S. PATENT DOCUMENTS

2004/0144974 A1* 7/2004 Lee et al. .......................... 257/40
2010/0044689 A1 2/2010 Nishimura et al.
(Continued)

FOREIGN PATENT DOCUMENTS

JP 2010-097964 4/2010
KR 10-2011-0027635 3/2011
(Continued)

OTHER PUBLICATIONS

"Organic Electroluminescent Diodes" Tang, et al.; Applied Physics Letters 51, p. 913, 1987.

*Primary Examiner* — Gregory Clark
(74) *Attorney, Agent, or Firm* — McKenna Long & Aldridge LLP (57) ABSTRACT

The present invention provides an organic light emitting diode comprising a first electrode, a second electrode and an organic material layer of one or more layers disposed between the first electrode and the second electrode, in which the organic material layer comprises a light emitting layer, an organic material layer comprising the compound represented by Formula 1 is comprised between the first electrode and the light emitting layer, and the light emitting layer comprises a host comprising the compound represented by Formula 1 and a dopant.

8 Claims, 4 Drawing Sheets

(56) References Cited

U.S. PATENT DOCUMENTS

| | | |
|---|---|---|
| 2010/0301312 A1* | 12/2010 | Jinde et al. .................... 257/40 |
| 2011/0248247 A1 | 10/2011 | Matsumoto et al. |
| 2012/0091438 A1 | 4/2012 | Yabunouchi et al. |
| 2012/0161612 A1 | 6/2012 | Kim et al. |

FOREIGN PATENT DOCUMENTS

| | | |
|---|---|---|
| WO | 2008-123178 | 10/2008 |
| WO | 2009-081857 | 7/2009 |
| WO | 2010-114021 | 10/2010 |

* cited by examiner

ORGANIC LIGHT-EMITTING DIODE AND METHOD FOR MANUFACTURING SAME

This application is a Continuation Bypass of International Application No. PCT/KR2012/009866, filed Nov. 21, 2012, which claims priority to and the benefit of Korean Patent Application No. 10-2011-0141372, filed on Dec. 23, 2011, the disclosures of which are incorporated herein by reference in their entirety.

TECHNICAL FIELD

The present invention relates to an organic light emitting diode and a manufacturing method thereof. More particularly, the present invention relates to an organic light emitting diode which has excellent characteristics of high efficiency and long service life and a simple manufacturing process, and a manufacturing method thereof.

BACKGROUND ART

An organic light emitting diode is an electric diode that emits light through electric current by applied voltage. Tang et al. reported an organic light emitting diode having a good characteristic in a treatise [Applied Physics Letters 51, p. 913, 1987]. Further, an organic light emitting diode using a polymer material while using a structure of the organic light emitting diode disclosed in the treatise has also been developed.

Figure 1:
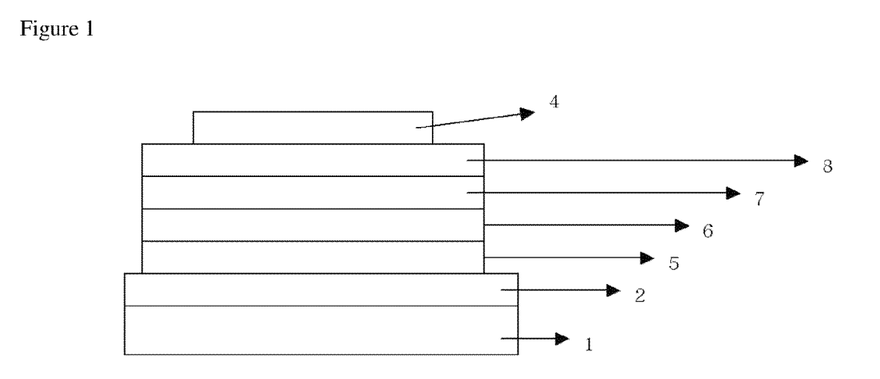
FIG. 1 illustrates an example of an organic light emitting diode comprising a substrate 1, a first electrode 2, a hole injection layer 5, a hole transporting layer 6, a light emitting layer 7, an electron transporting layer 8 and a second electrode 4.

The key point of the related art is to allow different organic material layers to share roles for performing processes in which the organic light emitting diode may emit light, such as charge injection, charge transport, formation of optical exciton and generation of light. Therefore, recently, as illustrated in FIG. 1, an organic light emitting diode comprising a first electrode 2, a hole injection layer 5, a hole transporting layer 6, a light emitting layer 7, an electron transporting layer 8 and a second electrode 4 or an organic light emitting diode having a segmented structure constituted by multiple layers has been used.

The organic light emitting diode is classified into a fluorescent OLED and a phosphorescent OLED (PhOLED) according to the emission type of light. In the PhOLED, light may be emitted from both singlet and triplet excitons. Therefore, the internal quantum efficiency reaches theoretically 100%, but in an actual diode, there is a problem in that light emission efficiency is significantly reduced due to injection loss of carriers, formation of non-luminescent excitons, triplet-triplet annihilation and the like.

DETAILED DESCRIPTION OF THE INVENTION

Technical Problem

Therefore, it is necessary to study an organic light emitting diode that may improve the light emission efficiency of the organic light emitting diode as described above and may be formed with a simpler structure.

Technical Solution

An exemplary embodiment of the present invention provides an organic light emitting diode comprising a first electrode, a second electrode and an organic material layer of one or more layers disposed between the first electrode and the second electrode, in which the organic material layer comprises a light emitting layer, an organic material layer comprising a compound represented by the following Formula 1 is comprised between the first electrode and the light emitting layer, and the light emitting layer comprises a host comprising a compound represented by the following Formula 1 and a dopant:

[Formula 1]

in Formula 1,

R1 to R10 are the same as or different from each other and are each independently selected from the group consisting of hydrogen, deuterium, halogen, an alkyl group having 1 to 10 carbon atoms, an alkenyl group having 2 to 10 carbon atoms, an alkoxy group having 1 to 10 carbon atoms, an aryl group having 6 to 20 carbon atoms, and a heteroaryl group having 5 to 20 carbon atoms, Ar1 and Ar2 are the same as or different from each other and are each independently selected from the group consisting of an aryl group having 6 to 20 carbon atoms and a heteroaryl group having 5 to 20 carbon atoms, and m and n are each independently an integer of 0 to 4.

Advantageous Effects

The organic light emitting diode according to the present invention comprises an organic material layer comprising the compound represented by Formula 1 between a first electrode and a light emitting layer, and the light emitting layer comprises the compound represented by Formula 1 as a light emitting host to transport holes injected from the first electrode through a hole transporting layer to the light emitting layer without energy barrier, thereby making it easy to transfer holes.

In addition, the mixing ratio of the compound represented by Formula 1 in the light emitting layer may be controlled to enhance the efficiency of producing excitons. Furthermore, an additional light emitting layer or electron/exciton prevention layer may not be used in order to reduce an effect that an exciton is transferred to an electron transporting layer and light is not emitted, and thus, an organic light emitting diode may be implemented by a simple and economical manufacturing process, compared to an organic light emitting diode in the related art.

BEST MODE

Hereinafter, the present invention will be described in detail.

In order to sufficiently understand the present invention, the operational advantages of the present invention, and the objectives achieved by the embodiments of the present invention, the accompanying drawings illustrating preferred embodiments of the present invention and the contents described therein need to be referred to. Hereinafter, the present invention will be described in detail by explaining preferred embodiments of the present invention with reference to the accompanying drawings. In each of the drawings, like reference numerals denote like elements.

The terms used in the present specification are for explaining the embodiments rather than limiting the present invention. Unless particularly stated otherwise in the present specification, a singular form also comprises a plural form. The word "comprises" and/or "comprising" used in the present specification will be understood to imply the inclusion of stated constituents, steps, operations and/or elements but not the exclusion of any other constituents, steps, operations and/or elements.

In order to suppress the light emission efficiency of an organic light emitting diode from being reduced, a host having hole transporting characteristics and a host having electron transporting characteristics may be co-deposited with a light emitting dopant to improve the efficiency and service life of the phosphorescent light emitting diode. A plural host co-deposition mode may allow the amount of holes and electrons received in a light emitting layer to be controlled even though the light emitting layer may be formed while a mixing ratio of host materials having different characteristics is varied, and thus holes and electrons moving from a hole transporting layer and an electron transporting layer to a light emitting layer are not transferred to the light emitting layer at the same ratio. The phosphorescent light emitting layer co-deposited at an appropriate ratio may balance holes and electrons in the light emitting layer to shift a region in which excitons are formed mainly to the light emitting layer and reduce the probability that the excitons are released from the light emitting layer and annihilated without emission of light, thereby improving the efficiency. Further, the concentration may be sufficient for excitons to be formed uniformly throughout the entire light emitting layer and the triplet-triplet annihilation probability is also reduced, thereby improving the efficiency.

Such a structure is a method of improving the efficiency by controlling the charge balance in accordance with the minor carrier within an amount of charges transferred from the light emitting layer itself to the hole and electron injection layer, and thus holes (or electrons) supplied in an excessive amount compared to electrons (or holes) may not contribute to light emission in the entire diode. In order to improve a part in which either one of the holes or electrons are supplied with an excessive charge and fail to contribute to the light emission, it is possible to selectively insert a light emitting layer in which a hole transportable host is used in the front and back of the light emitting layer formed by co-depositing a plurality of hosts, or a light emitting layer in which an electron transportable host is used.

In addition, the hole injection ability may be modified by the HOMO energy barrier of the light emitting layer that is in contact with the hole transporting layer. When a hole transporting material used in the co-deposited light emitting layer is used as a hole transporting layer, the HOMO energy barrier between the hole transporting layer and the light emitting layer disappears, and thus holes are injected more easily into the light emitting layer. Accordingly, the probability of producing an exciton of an excessive electron and an injection strengthened hole may be increased to improve the diode efficiency. In addition, excessive electrons which fail to contribute to light emission lose energy while emitting light in the light emitting layer, and the degree of contributing to the deterioration of the hole transporting layer is decreased, thereby exhibiting an effect on the improvement in the service life of the diode.

Therefore, in order to solve the difficulty in a complicated diode structure or a process caused by the structure, the present invention is intended to provide a diode structure which utilizes the advantage of a plural host light emitting structure and simplifies a process while a hole transportable host is used as a host transporting material for a diode to which electrons are supplied in a larger amount than that of holes to facilitate the supply of holes to the light emitting layer.

FIG. 1 is a structural view illustrating the stacking structure of the phosphorescent organic light emitting diode according to a specific example of the present invention.

The organic light emitting diode according to the present invention comprises a first electrode, a second electrode and an organic material layer of one or more layers disposed between the first electrode and the second electrode, in which the organic material layer comprises a light emitting layer, an organic material layer comprising the compound represented by Formula 1 is comprised between the first electrode and the light emitting layer, and the light emitting layer comprises a host comprising the compound represented by Formula 1 and a dopant.

In the organic light emitting diode according to the present invention, it is preferred that the organic material layer comprising the compound represented by Formula 1 between the first electrode and the light emitting layer is in contact with the light emitting layer, but it is not limited thereto.

An additional organic material layer may be comprised between the organic material layer comprising the compound represented by Formula 1 between the first electrode and a light emitting layer, and the light emitting layer. For example, an organic material layer capable of serving a role as a layer of blocking an exciton may be additionally comprised, but it is not limited thereto.

In the organic light emitting diode according to the present invention, the organic material layer comprising the compound represented by Formula 1 between the first electrode and the light emitting layer may be a hole transporting layer.

The hole transporting layer and the light emitting layer may comprise the compound represented by Formula 1 to serve as a role of effectively transferring holes to the light emitting layer.

The hole transporting layer comprising the compound represented by Formula 1 is in contact with the light emitting layer to effectively transfer holes flowing from the first electrode to the light emitting layer, and when the ratio of the compound represented by Formula 1 in the light emitting layer is controlled, the probability of producing an exciton in the light emitting layer is increased and may be controlled such that the excitons produced are uniformly spread throughout the entire light emitting layer and formed. In this case, excitons fail to contribute to light emission and flow into the adjacent electron transporting layer to reduce the probability that excitons emit no light and are annihilated and thus the light emission efficiency is improved, and excitons are concentrated at one side to prevent the effect of accelerating the aging of the specific portion in the light emitting layer, thereby implementing an organic light emitting diode with the service life improved.

In the organic light emitting diode according to the present invention, the compound represented by Formula 1 to be comprised in an organic material layer between the first electrode and the light emitting layer and the compound represented by Formula 1 to be comprised in the light emitting layer may be the same compound.

In the organic light emitting diode according to the present invention, the substituent groups of Formula 1 will be described in more detail as follows.

Examples of the halogen group comprise fluorine, chlorine, bromine, iodine and the like, but are not limited thereto.

The alkyl group may be straight-chained or branch-chained, and specific examples thereof comprise a methyl group, an ethyl group, a propyl group, an isopropyl group, a butyl group, a t-butyl group, a pentyl group, a hexyl group, a heptyl group and the like, but are not limited thereto.

The alkenyl group may be straight-chained or branch-chained, and specific examples thereof comprise an alkenyl group linked with an aryl group such as a stylbenzyl group, a styrenyl group and the like, but are not limited thereto.

Examples of the alkoxy group comprise a methoxy group, an ethoxy group, an isopropyloxy group and the like, but are not limited thereto.

The aryl group may be a monocyclic type or a polycyclic type. Examples of the monocyclic aryl group comprise a phenyl group, a biphenyl group, a terphenyl group, a stilbene group and the like, examples of the polycyclic aryl group comprise a naphthyl group, an anthracenyl group, a phenanthrene group, a pyrenyl group, a perylenyl group, a chrysenyl group and the like, but these examples are not limited thereto.

The heteroaryl group is a ring group comprising O, N, S or P as a heteroatom, examples of the heterocyclic group comprise a carbazole group, a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, an acridyl group and the like, and compounds having the following structural formulas are preferred, but are not limited thereto.

Further, in the present specification, the term "substituted or unsubstituted" means that a group is substituted with one or more substituent groups selected from the group consisting of deuterium, a halogen group, an alkyl group, an alkenyl group, an alkoxy group, a silyl group, an arylalkenyl group, an aryl group, a heteroaryl group, a carbazole group, an arylamine group, a fluorenyl group which is unsubstituted or substituted with an aryl group, and a nitrile group, or does not have any substituent group.

R1 to R10 and Ar1 and Ar2 in Formula 1 may be further substituted with an additional substituent group, and specific examples thereof comprise a halogen group, an alkyl group, an alkenyl group, an alkoxy group, a silyl group, an arylalkenyl group, an aryl group, a heteroaryl group, a carbazole group, an arylamine group, a fluorenyl group which is unsubstituted or substituted with an aryl group, a nitrile group, and the like, but are not limited thereto.

The compound represented by Formula 1 may be preferably selected from the group consisting of the following structural formulas.

Formula 1-1

Formula 1-2

Formula 1-3

Formula 1-4

-continued

Formula 1-5

Formula 1-6

Formula 1-7

Formula 1-8

Formula 1-9

Formula 1-10

In the organic light emitting diode according to the present invention, the light emitting layer may additionally comprise, as a host, one or more among the compounds represented by the following Formulas 2 to 4 in addition to the compound represented by Formula 1.

[Formula 2]

in Formula 2,

X1 to X3 are independently CH or N, and at least one of X1 to X3 is N,

Ar3 to Ar5 are the same as or different from each other and are each independently selected from the group consisting of an aryl group having 6 to 20 carbon atoms and a heteroaryl group having 5 to 20 carbon atoms, and Ar4 and Ar5 may be combined with a ring comprising X to form a condensed ring.

[Formula 3]

in Formula 3,

Ar6 to Ar9 are the same as or different from each other and are each independently selected from the group consisting of an aryl group having 6 to 20 carbon atoms and a heteroaryl group having 5 to 20 carbon atoms, and Ar6 and Ar7, or Ar8 and Ar9 may be directly linked to each other, or combined with each other to form a condensed or uncondensed ring.

[Formula 4]

in Formula 4,

Ar10 to Ar12 are the same as or different from each other and are each independently selected from the group consisting of an aryl group having 6 to 20 carbon atoms and a heteroaryl group having 5 to 20 carbon atoms, and

Adjacent groups in Ar10 to Ar12 may be combined with each other to form a condensed or uncondensed ring.

In the organic light emitting diode according to the present invention, the weight ratio of the compound represented by

Formula 1 to one or more among the compounds represented by Formulas 2 to 4 may be 1:19 to 19:1, but is not limited thereto.

In the organic light emitting diode according to the present invention, the content of the host in the light emitting layer may be 80% by weight to 99% by weight, and the content of the dopant in the light emitting layer may be 1% by weight to 20% by weight. Here, the content of the host and the dopant in the light emitting layer is based on the total weight of materials constituting the light emitting layer.

The compound represented by Formula 2 may be preferably selected from the group consisting of the following structural formulas.

The compound represented by Formula 3 may be preferably selected from the group consisting of the following structural formulas.

The compound represented by Formula 4 may be preferably selected from the group consisting of the following structural formulas.

The organic light emitting diode of the present invention may be prepared by typical manufacturing methods of organic light emitting diode and materials except for using the above-described compounds to form an organic material layer of two or more layers.

The compound represented by the Formula 1 may be used to form an organic material layer by using a vacuum deposition method as well as a solution coating method during the manufacture of an organic light emitting diode. Herein, the solution coating method means spin coating, dip coating, inkjet printing, screen printing, a spray method, roll coating and the like, but is not limited thereto.

The organic material layer of the organic light emitting diode of the present invention may be composed of a multi-layered structure in which the organic material layers of two or more layers are stacked. For example, the organic light emitting diode of the present invention may have a structure comprising a hole injection layer, a hole transporting layer, a light emitting layer, an electron transporting layer, an electron injection layer and the like as an organic material layer. However, the structure of the organic light emitting diode is not limited thereto, and may comprise the fewer number or larger number of organic material layers.

For example, the organic light emitting diode of the present invention may have a structure shown in FIG. 1, but is not limited thereto.

In FIG. 1, the structure of an organic light emitting diode, in which an anode 2, a hole injection layer 5, a hole transporting layer 6, a light emitting layer 7, an electron transporting layer 8, and a cathode 4 are sequentially stacked on a substrate 1, is illustrated. In the structure, the compound represented by Formula 1 may be comprised in the hole transporting layer 6 and the light emitting layer 7.

For example, the organic light emitting diode according to the present invention may be manufactured by depositing a metal or a metal oxide having conductivity, or an alloy thereof on a substrate to form an anode by a physical vapor deposition (PVD) method such as sputtering or e-beam evaporation, forming an organic material layer which comprises a hole injection layer, a hole transporting layer, a light emitting layer, and an electron transporting layer thereon, and then depositing a material which may be used as the cathode thereon. In addition to these methods, an organic light emitting diode may also be manufactured by sequentially depositing an organic material layer from a cathode material, and an anode material on a substrate.

Further, the organic material layer may be manufactured with fewer number of layers by using various polymer materials by a solvent process other than a deposition method, and methods, such as, for example, spin coating, dip coating, doctor blading, screen printing, inkjet printing, a thermal transfer method or the like.

It is preferred that as the anode material, materials having a high work function are usually used so as to facilitate the injection of holes into the organic material layer. Specific examples of the anode material which may be used in the present invention comprise metals such as vanadium, chromium, copper, zinc, and gold, or alloys thereof; metal oxides such as zinc oxide, indium oxide, indium tin oxide (ITO), and indium zinc oxide (IZO); a combination of metal and oxide, such as $ZnO:Al$ or $SnO_2:Sb$; and electrically conductive polymers, such as poly(3-methylcompound), poly[3,4-(ethylene-1,2-dioxy)compound](PEDT), polypyrrole, and polyaniline, and the like, but are not limited thereto.

It is preferred that as the cathode material, materials having a low work function are usually used so as to facilitate the injection of electrons into the organic material layer. Specific examples of the cathode material comprise metals such as magnesium, calcium, sodium, potassium, titanium, indium, yttrium, lithium, gadolinium, aluminum, silver, tin and lead, or alloys thereof; multi-layer structured materials such as LiF/Al or $LiO_2$/Al, and the like, but are not limited thereto.

The hole injection material is a material facilitating hole injection from the anode at low voltage, and the highest occupied molecular orbital (HOMO) of the hole injection material is preferably located between the work function of the anode material and the HOMO of the neighboring organic material layer of the material. Specific examples of the hole injection material comprise metal porphyrine, oligothiophene, arylamine-based organic materials, hexanitrile hexaazatriphenylene-based organic materials, quinacridone-based organic materials, perylene-based organic materials, antraquinone, and polyaniline-based and polycompound-based conductive polymers, and the like, but are not limited thereto.

The electron transporting material is suitably a material having high electron mobility, which may accept and transfer electrons from the cathode to the light emitting layer. Specific examples thereof comprise aluminum complexes of 8-hydroxyquinoline; complexes comprising $Alq_3$; organic radical compounds; hydroxyflavone-metal complexes, and the like, but are not limited thereto.

The organic light emitting diode according to the present invention may be of a front emission type, a rear emission type or a dual emission type according to the materials used. In addition, the organic light emitting diode according to the present invention may have a constant structure in which the lower electrode is an anode and the upper electrode is a cathode and a reverse structure in which the lower electrode is a cathode and the upper electrode is an anode.

The compound according to the present invention may act by a principle, which is similar to that applied to organic light emitting diodes, to organic electronic diodes comprising organic solar cells, organic photoreceptors, organic transistors, and the like.

Best Mode

Hereinafter, the present invention will be described in more detail with reference to Examples. However, the following Examples are set forth to illustrate the present invention but are not intended to limit the scope of the present invention.

EXAMPLES

Compounds used in Examples and Comparative Examples are as follows.

[cp1]

[cp2]

[cp3]

[cp4]

[cp5]

[cp6]

-continued

[cp7]

Comparative Example 1

A transparent electrode (Indium Tin Oxide) was deposited as a hole injection electrode to a thickness of 100 nm on a glass substrate, and was subjected to oxygen plasma treatment at a pressure of 30 mTorr and a power of 80 w for 30 seconds. [cp1] was deposited to a thickness of 30 nm thereon by heating the compound [cp1] in vacuum. [cp2] was deposited to a thickness of 40 nm as a hole transporting layer thereon. [cp3] belonging to Formula 2 was deposited as a light emitting layer to a thickness of 40 nm thereon, and [cp6] was doped as a light emitting dopant by 16%. Subsequently, an organic light emitting diode was manufactured by depositing [cp5] as an electron transporting and injection layer to a thickness of 20 nm thereon, depositing LiF as an electron injection layer to a thickness of 1 nm thereon, and depositing Al as an electron injection electrode to a thickness of 150 nm thereon.

Comparative Example 2

An organic light emitting diode was manufactured in the same manner as in Comparative Example 1, except that [cp4] belonging to Formula 3 was used instead of [cp3] as the light emitting layer in Comparative Example 1.

Comparative Example 3

An organic light emitting diode was manufactured in the same manner as in Comparative Example 1, except that [cp5] belonging to Formula 4 was used instead of [cp3] as the light emitting layer in Comparative Example 1.

Comparative Example 4

An organic light emitting diode was manufactured in the same manner as in Comparative Example 1, except that a compound of Formula 1-5 was used instead of [cp3] as the light emitting layer in Comparative Example 1.

Comparative Example 5

An organic light emitting diode was manufactured in the same manner as in Comparative Example 1, except that a compound of Formula 1-2 was used instead of [cp3] as the light emitting layer in Comparative Example 1.

Example 1

An organic light emitting diode was manufactured in the same manner as in Comparative Example 1, except that a compound of Formula 1-5 was deposited to a thickness of 40 nm instead of [cp2] as a hole transporting layer in Comparative Example 1.

Example 2

An organic light emitting diode was manufactured in the same manner as in Example 1, except that a compound of Formula 1-5 and [cp3] were mixed at a ratio of 1:1 to form a film on the light emitting layer in Example 1.

Example 3

An organic light emitting diode was manufactured in the same manner as in Example 1, except that a compound of Formula [cp4] was deposited to a thickness of 40 nm instead of [cp3] as the light emitting layer in Example 1.

Example 4

An organic light emitting diode was manufactured in the same manner as in Example 3, except that a compound of Formula 1-5 and [cp4] were mixed at a ratio of 1:1 to form a film on the light emitting layer in Example 3.

Example 5

An organic light emitting diode was manufactured in the same manner as in Example 1, except that a compound of Formula [cp5] was deposited to a thickness of 40 nm instead of [cp3] as the light emitting layer in Example 1.

Example 6

An organic light emitting diode was manufactured in the same manner as in Example 5, except that a compound of Formula 1-5 and [cp5] were mixed at a ratio of 1:1 to form a film on the light emitting layer in Example 5.

Example 7

An organic light emitting diode was manufactured in the same manner as in Comparative Example 1, except that a compound of Formula 1-2 was used instead of [cp2] as the hole transporting layer and a compound of Formula 1-2 and [cp3] were mixed at a ratio of 1:1 to form a film on the light emitting layer in Comparative Example 1.

Example 8

An organic light emitting diode was manufactured in the same manner as in Comparative Example 2, except that a compound of Formula 1-2 was used instead of [cp2] as the hole transporting layer and a compound of Formula 1-2 and [cp4] were mixed at a ratio of 1:1 to form a film on the light emitting layer in Comparative Example 2.

Example 9

An organic light emitting diode was manufactured in the same manner as in Comparative Example 3, except that a compound of Formula 1-2 was used instead of [cp2] as the hole transporting layer and a compound of Formula 1-2 and [cp5] were mixed at a ratio of 1:1 to form a film on the light emitting layer in Comparative Example 3.

Example 10

An organic light emitting diode was manufactured in the same manner as in Example 1, except that a compound of Formula 1-5 and [cp3] were mixed at a ratio of 0.1:0.9 to form a film on the light emitting layer in Example 2.

Example 11

An organic light emitting diode was manufactured in the same manner as in Example 1, except that a compound of Formula 1-5 and [cp3] were mixed at a ratio of 0.9:0.1 to form a film on the light emitting layer in Example 2.

Example 12

An organic light emitting diode was manufactured in the same manner as in Example 1, except that a compound of Formula 1-2 and [cp3] were mixed at a ratio of 0.1:0.9 to form a film on the light emitting layer in Example 7.

Example 13

An organic light emitting diode was manufactured in the same manner as in Example 1, except that a compound of Formula 1-2 and [cp3] were mixed at a ratio of 0.9:0.1 to form a film on the light emitting layer in Example 7.

Characteristics of the diode manufactured at a current density of 20 mA/cm$^2$ are as the following Table 1.

Figure 2:
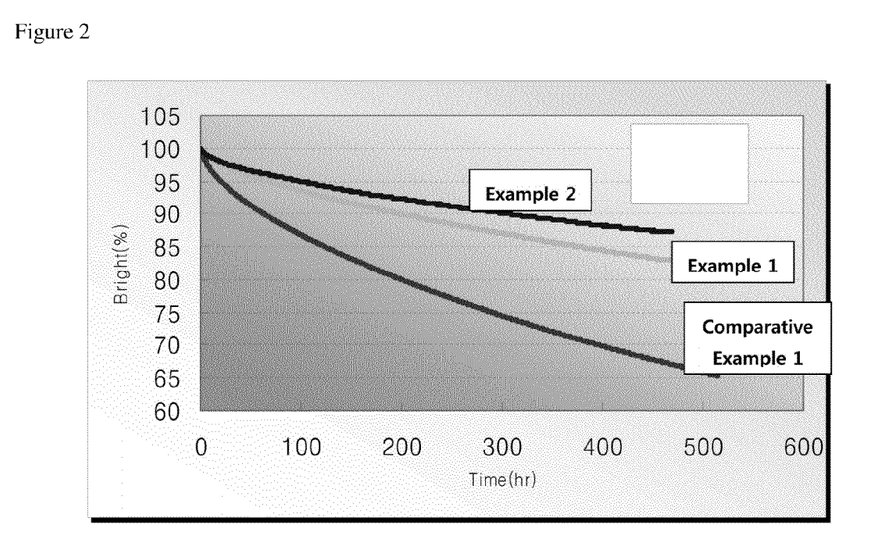
FIG. 2 is a graph comparing the luminance reduction curves obtained during the driving of the diodes in Comparative Example 1 and Examples 1 and 2 at a current density of 20 mA/cm$^2$.
Figure 3:
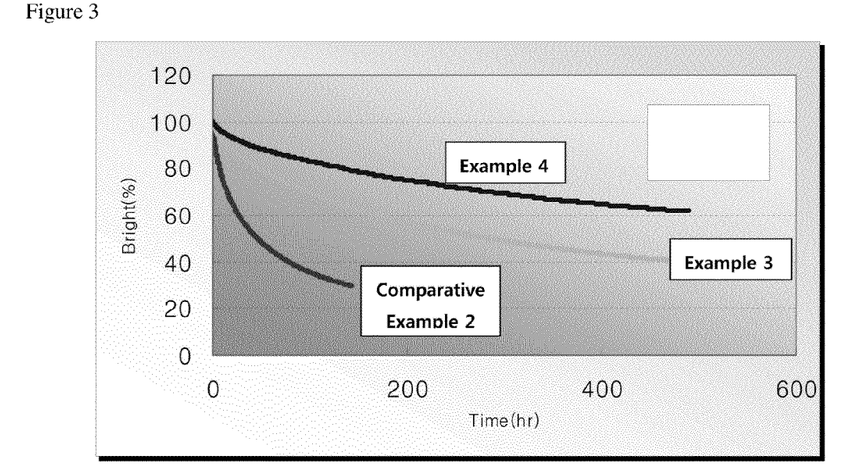
FIG. 3 is a graph comparing the luminance reduction curves obtained during the driving of the diodes in Comparative Example 2 and Examples 3 and 4 at a current density of 20 mA/cm².
Figure 4:
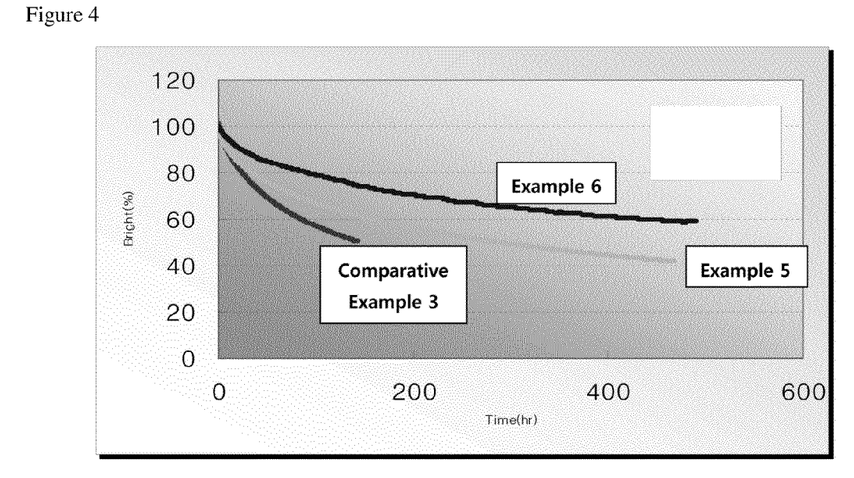
FIG. 4 is a graph comparing the luminance reduction curves obtained during the driving of the diodes in Comparative Example 3 and Examples 5 and 6 at a current density of 20 mA/cm².

Furthermore, FIG. 2 illustrates a graph comparing the luminance reduction curves obtained during the driving of the diodes in Comparative Example 1 and Examples 1 and 2 at a current density of 20 mA/cm$^2$. Further, FIG. 3 illustrates a graph comparing the luminance reduction curves obtained during the driving of the diodes in Comparative Example 2 and Examples 3 and 4 at a current density of 20 mA/cm$^2$. In addition, FIG. 4 illustrates a graph comparing the luminance reduction curves obtained during the driving of the diodes in Comparative Example 3 and Examples 5 and 6 at a current density of 20 mA/cm$^2$.

Figure 5:
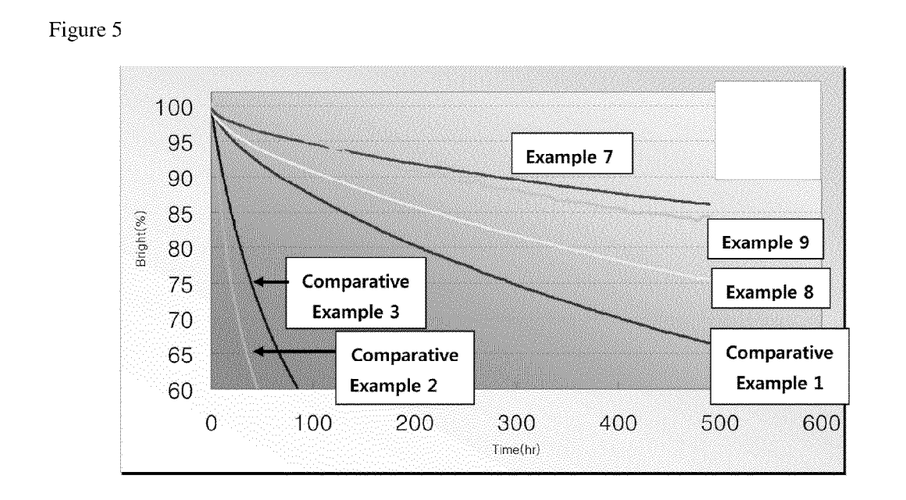
FIG. 5 is a graph comparing the luminance reduction curves obtained during the driving of the diodes in Comparative Examples 1, 2 and 3 and Examples 7, 8 and 9 at a current density of 20 mA/cm².

FIG. 5 illustrates a graph comparing the luminance reduction curves obtained during the driving of the diodes in Comparative Examples 1, 2 and 3 and Examples 7, 8 and 9 at a current density of 20 mA/cm$^2$.

Figure 6:
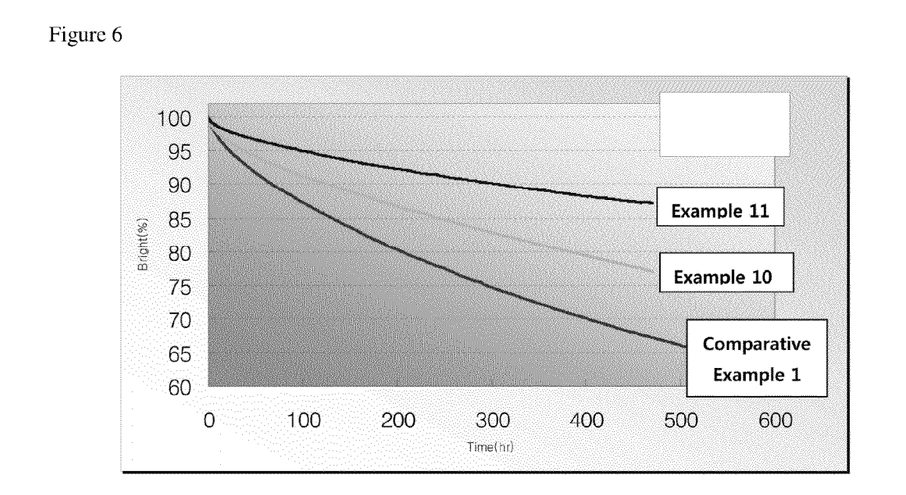
FIG. 6 is a graph comparing the luminance reduction curves obtained during the driving of the diodes in Comparative Example 1 and Examples 10 and 11 at a current density of 20 mA/cm².

FIG. 6 illustrates a graph comparing the luminance reduction curves obtained during the driving of the diodes in Comparative Example 1 and Examples 10 and 11 at a current density of 20 mA/cm$^2$.

Figure 7:
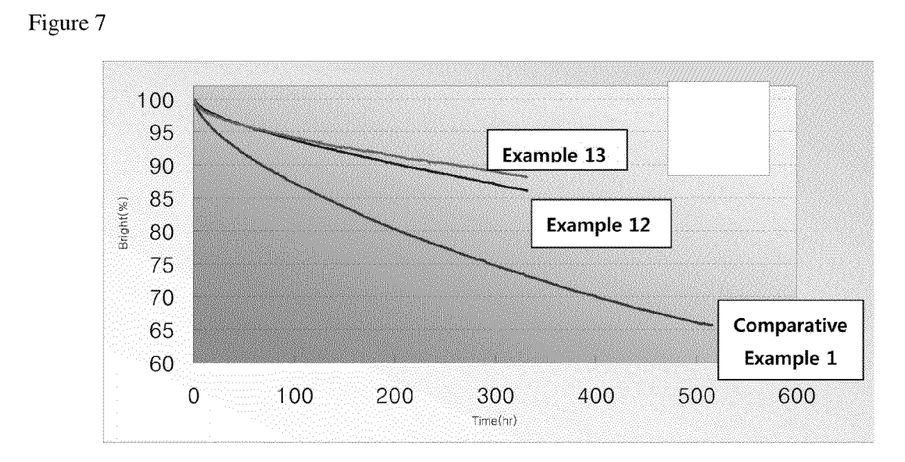
FIG. 7 is a graph comparing the luminance reduction curves obtained during the driving of the diodes in Comparative Example 1 and Examples 12 and 13 at a current density of 20 mA/cm².

FIG. 7 illustrates a graph comparing the luminance reduction curves obtained during the driving of the diodes in Comparative Example 1 and Examples 12 and 13 at a current density of 20 mA/cm$^2$.

TABLE 1

| Division | V | Cd/A | Lm/W |
|---|---|---|---|
| Comparative Example 1 | 4.5 | 35.7 | 24.8 |
| Comparative Example 2 | 6.0 | 2.5 | 1.3 |
| Comparative Example 3 | 5.7 | 16.6 | 9.2 |
| Comparative Example 4 | 6.4 | 20.8 | 10.2 |
| Comparative Example 5 | 5.4 | 22.4 | 11.0 |
| Example 1 | 5.0 | 38.5 | 24.0 |
| Example 2 | 5.3 | 43.0 | 25.1 |
| Example 3 | 5.2 | 37.4 | 22.8 |
| Example 4 | 5.2 | 38.6 | 23.4 |
| Example 5 | 6.1 | 39.0 | 20.0 |
| Example 6 | 5.3 | 40.5 | 24.5 |
| Example 7 | 4.7 | 39.1 | 26.1 |
| Example 8 | 4.7 | 39.8 | 26.6 |
| Example 9 | 5.1 | 38.3 | 23.8 |
| Example 10 | 4.9 | 39.4 | 25.2 |
| Example 11 | 5.2 | 37.1 | 22.4 |
| Example 12 | 4.7 | 39.9 | 26.7 |
| Example 13 | 4.4 | 39.2 | 27.8 |

When Example 1 in which a material of Formula 1 was used as a hole transporting material is compared with Comparative Example 1 in which a material of Formula 1 was not used, the efficiency increased by 8% in comparison with that in Example 1, and in the case of Example 2 in which a material of Formula 1 was used as a hole transporting material and was used as a mixed host in the light emitting layer, the efficiency increased by 20% or more in comparison with that in Comparative Example 1.

In addition, as known from FIG. 2, it can be known that Example 1 in which a compound of Formula 1 was used as a hole transporting layer had an improved service life compared to Comparative Example 1 in which a compound of Formula 1 was not used as a hole transporting layer, and Example 2 in which a compound of Formula 1 was simultaneously used as a hole transporting layer and a mixed light emitting host had a better service life improvement effect.

When compared to the case in which another light emitting host was used, it can be seen that when [cp4] was used instead of [cp3], only efficiency of 2.5 cd/A was produced in the case of Comparative Example 2 in which a material of Formula 1 was not used as a hole transporting material, but the efficiency was sharply increased to 37.4 cd/A in Example 3 when a material of Formula 1 was used as a hole transporting material. This is due to the fact that when [cp2] was used as a hole transporting material and [cp4] was used as a light emitting layer host in Comparative Example 2, electron transporting ability of [cp4] was much better than that of [cp3] and thus electrons introduced from the cathode failed to contribute to light emission in the light emitting layer and passed over to [cp2] which is a hole transporting layer, thereby causing a situation that the charge balance between holes and electrons was broken while [cp2] rather emitted light.

Example 4 in which the material of Formula 1 was applied as a hole transporting layer and a mixed light emitting host showed much better light emission efficiency than that of Comparative Example 2, and also showed an efficiency increasing effect by a small margin than that in Example 3. Furthermore, as known from FIG. 3, it can be known that Example 3 in which a compound of Formula 1 was used as a hole transporting layer had a significantly improved service life compared to Comparative Example 2 in which a compound of Formula 1 was not used as a hole transporting layer, and Example 4 in which a compound of Formula 1 was used simultaneously as a hole transporting layer and a mixed light emitting host had a better service life improvement effect.

When compared to the case in which yet another light emitting host was used, it can be seen that when [cp5] was used instead of [cp3], only efficiency of 16.6 cd/A was produced in the case of Comparative Example 3 in which a material of Formula 1 was not used as a hole transporting material, but the efficiency was sharply increased to 39.0 cd/A by two times or more in Example 5 when a material of Formula 1 was used as a hole transporting material. This is due to the fact that when [cp2] was used as a hole transporting material and [cp5] was used as a light emitting layer host in Comparative Example 3, electron transporting ability of [cp5] was much better than that of [cp3] and thus electrons introduced from the cathode failed to contribute to light emission in the light emitting layer and passed over to [cp2] which is a hole transporting layer, thereby causing a situation that the charge balance between holes and electrons was broken while [cp2] rather emitted light.

Further, according to Comparative Examples 4 and 5 in which a material of Formula 1 was used as a light emitting host and a compound of Formula 1 of the present invention was not used as a hole transporting material, it can be known that the efficiencies are only 20.8 cd/A and 22.4 cd/A, respectively. Therefore, it can be known that the Examples, in which a compound of Formula 1 of the present invention was used simultaneously as a hole transporting layer and a mixed light emitting host, had a much better service life improvement effect.

Example 6 in which the material of Formula 1 was applied as a hole transporting layer and a mixed light emitting host showed much better light emission efficiency than that of Comparative Example 3, and also showed an efficiency increasing effect by a small margin than that in Example 5. In addition, as known from FIG. 4, it can be known that Example 5 in which a compound of Formula 1 was used as a hole transporting layer had a significantly improved service life compared to Comparative Example 3 in which a compound of Formula 1 was not used as a hole transporting layer, and Example 6 in which a compound of Formula 1 was used simultaneously as a hole transporting layer and a mixed light emitting host had a better service life improvement effect.

The hole transporting layer and light emitting layer comprising the compound represented by Formula 1 are in contact with each other to effectively transfer holes flowing from the first electrode to the light emitting layer to increase the ratio of producing an exciton in the light emitting layer, the compound represented by Formula 1 has hole transferable characteristics compared to [cp3], [cp4] and [cp5] which are other mixed host materials, and thus acts as a resistance against electrons in the light emitting layer and helps holes to flow well, and as a result, the compound effectively acts to bring about an increase in efficiency, such that excitons are produced uniformly throughout the entire light emitting layer, while excitons are produced mainly at an interface between the hole transporting layer and the light emitting layer when materials [cp3], [cp4] and [cp5] which are electron transferable host materials in the related art are only used.

Furthermore, by mixing and using a compound of Formula 1 having hole transfer characteristics in the light emitting layer, an exciton production position is spread throughout the entire light emitting layer to prevent the aging of a specific site, thereby showing a significant service life improvement effect, compared to the case in which only a material such as [cp3], [cp4] or [cp5] producing excitons in a specific position in the light emitting layer is used as a light emitting host material.

Further, Examples 7, 8 and 9 in which the material of Formula 1 was applied as a hole transporting layer and a mixed light emitting host show much better light emission efficiency than those of Comparative Examples 1, 2 and 3. In addition, as known from FIG. 5, it can be known that the case in which the material of Formula 1 is used as a hole transporting layer and a mixed light emitting host shows a much better service life improvement effect.

Furthermore, Examples 10, 11, 12 and 13 in which the material of Formula 1 was applied as a hole transporting layer and a mixed light emitting host show much better light emission efficiency than that of Comparative Example 1 by controlling the content ratio of the mixed light emitting hosts. The description may be confirmed even in FIGS. 6 and 7.

The invention claimed is:

1. An organic light emitting diode, comprising:
   a first electrode;
   a second electrode; and
   an organic material layer of one or more layers disposed between the first electrode and the second electrode,
   wherein the organic material layer comprises a light emitting layer,
   an organic material layer comprising a compound represented by the following Formula 1 is comprised between the first electrode and the light emitting layer, and
   the light emitting layer comprises a host comprising a compound represented by the following Formula 1 and a dopant:

[Formula 1]

in Formula 1,
R1 to R10 are the same as or different from each other and are each independently selected from the group consisting of hydrogen, deuterium, halogen, an alkyl group having 1 to 10 carbon atoms, an alkenyl group having 2 to 10 carbon atoms, an alkoxy group having 1 to 10 carbon atoms, an aryl group having 6 to 20 carbon atoms, and a heteroaryl group having 5 to 20 carbon atoms,
Ar1 and Ar2 are the same as or different from each other and are each independently an aryl group having 6 to 20 carbon atoms and m and n are each independently an integer of 0 to 4.

2. The organic light emitting diode of claim 1, wherein the organic material layer comprising the compound represented by Formula 1 between the first electrode and the light emitting layer is in contact with the light emitting layer.

3. The organic light emitting diode of claim 1, wherein the organic material layer comprising the compound represented by Formula 1 between the first electrode and the light emitting layer is a hole transporting layer.

4. The organic light emitting diode of claim 3, further comprising:
   a hole injection layer between the first electrode and the hole transporting layer.

5. The organic light emitting diode of claim 1, wherein the compound represented by Formula 1 comprised in the organic material layer between the first electrode and the light emitting layer and the compound represented by Formula 1 comprised in the light emitting layer are the same material.

6. The organic light emitting diode of claim 1, wherein the compound represented by Formula 1 is selected from the group consisting of the following structural formulas:

Formula 1-1

Formula 1-2

Formula 1-3

Formula 1-4

-continued

Formula 1-5

Formula 1-6

Formula 1-7

Formula 1-8

Formula 1-9

Formula 1-10

7. The organic light emitting diode of claim 1, wherein a content of the host in the light emitting layer is 80% by weight to 99% by weight and a content of the dopant in the light emitting layer is 1% by weight to 20% by weight.

8. The organic light emitting diode of claim 1, wherein one or more organic material layers selected from the group consisting of an electron transporting layer, an electron injection layer and a layer simultaneously performing the transport and injection of electrons are comprised between the second electrode and the light emitting layer.

* * * * *